United States Patent
Lan et al.

(10) Patent No.: US 6,479,484 B1
(45) Date of Patent: Nov. 12, 2002

(54) SUBSTITUTED 2-AMINOACETAMIDES AND THE USE THEREOF

(75) Inventors: Nancy C. Lan, South Pasadena, CA (US); Yan Wang, San Diego, CA (US); Sui Xiong Cai, San Diego, CA (US)

(73) Assignee: Euro-Celtique S.A. (LU)

( * ) Notice: Subject to any disclaimer, the term of this patent is extended or adjusted under 35 U.S.C. 154(b) by 0 days.

(21) Appl. No.: 09/554,739

(22) PCT Filed: Nov. 20, 1998

(86) PCT No.: PCT/US98/24965

§ 371 (c)(1),
(2), (4) Date: Aug. 8, 2000

(87) PCT Pub. No.: WO99/26614

PCT Pub. Date: Jun. 3, 1999

Related U.S. Application Data

(60) Provisional application No. 60/066,707, filed on Nov. 21, 1997.

(51) Int. Cl.⁷ .................. A61K 31/4965; A61K 31/517; A61K 31/472; A61K 31/5375
(52) U.S. Cl. ..................... 514/231.2; 514/618; 514/617; 514/622; 514/620; 514/621; 514/249; 514/252.02; 514/256; 514/258.1; 514/259.4; 514/234.8
(58) Field of Search ................................. 564/162, 164, 564/167, 169, 172; 514/618, 249, 617, 252.02, 622, 256, 620, 258.1, 621, 259.4, 231.2, 234.8; 544/283, 284, 237, 242, 349, 353, 336, 338; 546/102, 122, 134, 139, 138, 145, 152, 255, 266, 346, 329; 548/309.7, 306.4, 335.5; 549/223, 440, 429

(56) References Cited

U.S. PATENT DOCUMENTS

| | | | |
|---|---|---|---|
| 3,576,864 A | 4/1971 | Kuppuswamy | 260/554 |
| 4,725,608 A | 2/1988 | Nakaguchi et al. | 514/353 |
| 5,236,957 A | 8/1993 | Dostert et al. | 514/620 |
| 5,446,066 A | 8/1995 | Varasi et al. | 514/620 |
| 5,449,692 A | 9/1995 | Varasi et al. | 514/620 |
| 5,741,818 A | 4/1998 | Dimmock | 514/590 |
| 5,945,454 A | * 8/1999 | Peverello et al. | 514/620 |

FOREIGN PATENT DOCUMENTS

| | | |
|---|---|---|
| WO | WO 90/14334 | 11/1990 |
| WO | WO 96/40628 | 12/1996 |
| WO | WO 97/05102 | 2/1997 |
| WO | WO 98/19998 | 5/1998 |
| WO | WO 98/43964 | 10/1998 |
| WO | WO 98/47869 | 10/1998 |
| WO | WO 99/39712 | 8/1999 |

OTHER PUBLICATIONS

Anonymous, "Neurogen Licenses National Institutes of Health (NIH) anticonvulsants," *SCRIP World Pharmaceutical News* 1773:14 (1992).

Anonymous, "Cambridge NeuroScience's grant for channel blockers," *SCRIP World Pharmaceutical News* 1870:8 (1993).

Bensimon, G., et al., "A Controlled Trial of Riluzole in Amyotrphic Lateral Sclerosis," *New Engl. J. Med.* 330:585–591 (1994).

Brown, C.M., et al., "Neuroprotective properties of Lifarizine compared with those of other agents in a mouse model of focal cerebral ischaemia," *British J. Pharmacol.* 115:1425–1432 (1995).

Catterall, W.A., "Common modes of drug action on Na⁺channels: Local anesthetics, antiarrhythmics and anticonvulsants," *Trends Pharmacol. Sci.* 8:57–65 (1987).

Catterall, W.A., "Neurotoxins that Act on Voltage–Sensitive Sodium Channels in Excitable Membranes," *Ann. Rev. Pharmacol. Toxicol.* 20:15–43 (1980).

Catterall, W.A., "Structure and Function of Voltage–Sensitive Ion Channels," *Science* 242:50–61 (1988).

Denicoff, K.D., et al., "Efficacy of Carbamazepine Compared With Other Agents: A Clinical Practice Survey," *J. Clin.Psychiatry* 55:70–76 (1994).

Dimmock, J.R., et al., "(Aryloxy)aryl Semicarbazones and Related Compounds: A Novel Class of Anticonvulsant Agetns Possessing High Activity in the Maximal Electroshock Screen," *J. Med. Chem.* 39:3984–3997 (1996).

Graham, S.H., et al., "Neuroprotective Effects of a Use–Dependent Blocker of Voltage–Dependent Sodium Channels, BW619C89, in Rat Middle Cerebral Artery Occlusion," *J. Pharmacol. Exp. Ther.* 269:854–859 (1994).

Pevarello, P., et al., "Synthesis and Anticonvulsant Activity of a New Class of 2–[(Arylalkyl)amino] alkanamide Derivatives," *J. Med. Chem.* 41:579–590 (1998).

(List continued on next page.)

Primary Examiner—Richard L. Raymond
Assistant Examiner—Kahsay Habte
(74) Attorney, Agent, or Firm—Sterne, Kessler, Goldstein & Fox, P.L.L.C.

(57) ABSTRACT

The invention is directed to substituted 2-aminoacetamides represented by formula (II):

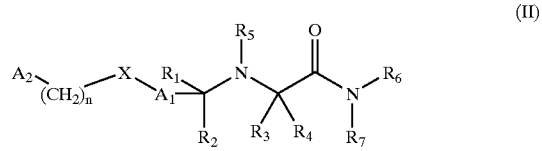

and to pharmaceutically acceptable salts and prodrugs thereof, wherein the substituents are defined herein. The invention is also directed to the use of substituted 2-aminoacetamides in methods for the treatment of neuronal damage following global and focal ischemia, and for the treatment, prevention or amelioration of pain, as anticonvulsants, as antimanic depressants, as local anesthetics, as antiarrhythmics and for the treatment or prevention of diabetic neuropathy.

19 Claims, No Drawings

OTHER PUBLICATIONS

Stys, P.K., et al., "Ionic Mechanism of Anoxic Injury in Mammalian CNS White Matter: Role of $Na^+$ Channels and $Na^+$–$Ca^{2+}$ Exchanger," *J. Neurosci.* 12:430–439 (1992).

Taylor, C.P. and Meldrum, B.S., "$Na^+$ channels as targets for neuroprotective drugs," *Trends Pharmacol. Sci.* 16:309–316 (1995).

International Search Report for PCT/US98/24965 (Mar. 1, 1999).

* cited by examiner

SUBSTITUTED 2-AMINOACETAMIDES AND THE USE THEREOF

This application is a 371 of PCT/US98/24965, filed Nov. 20, 1998 which claims benefit of Provisional Serial No. 60/066,707, filed Nov. 21, 1997.

BACKGROUND OF THE INVENTION

1. Field of the Invention

This invention is in the field of medicinal chemistry. In particular, the invention relates to substituted 2-aminoacetamides and the discovery that these compounds act as blockers of sodium ($Na^+$) channels.

2. Related Background Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W. A., *Trends Pharmacol. Sci.* 8:57–65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham et al., *J. Pharmacol. Exp. Ther.* 269:854–859 (1994); Brown et al., *British J. Pharmacol.* 115:1425–1432 (1995); *SCRIP* 1870:8 (1993); *SCRIP* 1773:14 (1992)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., *J. Neurosci.* 12:430–439 (1992)). Thus, they may offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensimm et al., *New Engl. J Med.* 330:585–591 (1994)) and has subsequently been approved by the FDA for the treatment of ALS. In addition to the above-mentioned clinical uses. carbamazepine, lidocaine and phenytoin are occasionally used to treat neuropathic pain, such as from trigeminal neurologia, diabetic neuropathy and other forms of nerve damage (Taylor and Meldrum, *Trends Pharmacol. Sci.* 16:309–316 (1995)), and carbamazepine and lamotrigine have been used for the treatment of manic depression (Denicott et al., *J. Clin. Psychiatry* 55: 70–76 (1994)).

It has been established that there are at least five to six sites on the voltage-sensitive $Na^+$ channels which bind neurotoxins specifically (Catterall, W. A., *Science* 242:50–61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., *Ann. Rev. Pharmacol. Toxicol.* 10:15–43 (1980)).

PCT International Published Application WO 90/14334 and WO 97/05102 disclose 2-(4-substituted)-benzylamino2-methyl-propanamide derivatives represented by Formula I: -

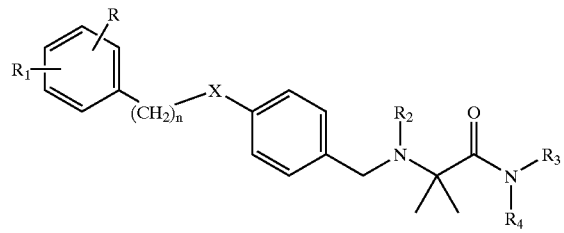

where n is 0–3; X is O, S, $CH_2$ or NH; each of R and $R_1$ independently is hydrogen, $C_{1-6}$ alkyl, halogen, hydroxy, $C_{1-4}$ alkoxy, or trifluoromethyl; each of $R_2$, $R_3$ and $R_4$ independently is hydrogen, $C_{1-6}$ alkyl or $C_{3-7}$ cycloalkyl; The compounds are disclosed to be useful as antiepileptics, in the treatment of Parkinson's disease and as neuroprotective agents, e.g. preventing or treating neuronal loss associated with stroke, hypoxia, ischemia, CNS trauma, hypoglycemia or surgery, and in treating and preventing neurodegenerative diseases such as Alzheimer's disease, amyotrophic lateral sclerosis, Down's syndrome, Huntington's disease, dementia caused by acquired immunodeficiency syndrome (AIDS), infarctual dementia and infections or inflammations in the brain; they can also be used as antidepressants, hypnotics, and antispastic agents and in treating ocular damage and retinopathy. However, their mechanism of action was not disclosed.

SUMMARY OF THE INVENTION

The present invention is related to treating a disorder responsive to the blockade of sodium channels in a mammal suffering from excess activity of said channels by administering an effective amount of a compound of Formula I. The present invention is also related to treating a disorder responsive to the blockade of sodium channels in a mammal suffering therefrom by administering an effective amount of a compound of Formula II as described herein.

The present invention is also directed to the use of a compound of Formulae I or II for the treatment of neuronal damage following global and focal ischemia, and for the treatment or prevention of neurodegenerative conditions such as amyotrophic lateral sclerosis (ALS), as antimanic depressants, as local anesthetics, as antiarrhythmics and for the treatment or prevention of diabetic neuropathy and for the treatment of pain including chronic pain.

The present invention also is directed to the process for preparing novel substituted 2-aminoacetamide of Formula II.

A first aspect of the present invention is directed to the use of compounds of Formulae I or II as blockers of sodium channels.

A second aspect of the present invention is to provide a method for treating, preventing or ameliorating neuronal loss following global and focal ischemia; treating, preventing or ameliorating pain including chronic pain; treating, preventing or ameliorating neurodegenerative conditions; treating, preventing or ameliorating manic depression; inducing local anesthesia; and treating arrhythmias by administering a compound of Formulae I or II to a mammal in need of such treatment.

A number of compounds within the scope of the present invention are novel compounds. Therefore, a third aspect of the present invention is to provide novel compounds of Formula II, and to also provide for the use of these novel compounds for treating, preventing or ameliorating convulsions.

A fourth aspect of the present invention is to provide a pharmaceutical composition useful for treating disorders responsive to the blockade of sodium ion channels, containing an effective amount of a compound of Formulae I or II in a mixture with one or more pharmaceutically acceptable carriers or diluents.

A fifth aspect of the present invention is directed to methods for preparing novel compounds of Formulae II.

DETAILED DESCRIPTION OF THE INVENTION

The present invention arises out of the discovery that compounds of Formulae I and II act as blocker of the $Na^+$ channel. In view of this discovery, compounds of Formulae I and II are useful for treating disorders responsive to the blockade of sodium ion channels.

The compounds useful in this aspect of the present invention are substituted 2-aminoacetamides represented by Formula II:

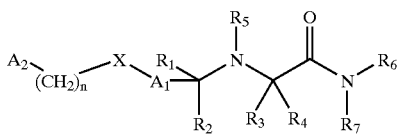

II or a pharmaceutically acceptable salt or prodrug thereof, wherein:

$R_1$ $R_2$, $R_3$ and $R_4$ are independently hydrogen, alkyl, cycloalkyl, alkenyl, alkynyl, haloalkyl, aryl, aminoalkyl, hydroxyalkyl, alkoxyalkyl or carboxyalkyl;

$R_5$, $R^6$ and $R_7$ are independently hydrogen, alkyl, cycloalkyl, alkenyl, alkynyl, haloalkyl, aryl, aminoalkyl, hydroxyalkyl, alkoxyalkyl or carboxyalkyl, or $R_5$, is defined as above, and $R_6$ and $R_7$ together with the nitrogen atom to which they are attached form a heterocycle;

$A_1$ and $A_2$ are independently aryl, heteroaryl, saturated or partially unsaturated carbocycle or saturated or partially unsaturated heterocycle, any of which is optionally substituted;

X is one or O, S, $NR_8$, $CH_2$, C(O), $NR_8C(O)$, $C(O)NR_8$, SO, $SO_2$ or a covalent bond; where $R_8$ is hydrogen, alkyl, cycloalkyl, alkenyl, alkynyl, haloalkyl, aryl, aminoalkyl, hydroxyalkyl, alkoxyalkyl or carboxyalkyl;

n is 0, 1, 2 or 3.

Preferred compounds falling within the scope of Formula II include compounds wherein $A_1$ and $A_2$ are both aryl moieties, preferably both phenyl moieties, that are each optionally independently substituted by one or two substituents independently selected from the group consisting of halogen, nitro, amino, $C_{1-6}$ alkyl, $C_{3-8}$ cycloalkyl, cyano, $C_{1-6}$ alkoxy or $C_{6-10}$ aryloxy; $R_1$ is hydrogen, $C_{1-6}$ alkyl, $C_{3-8}$ cycloalkyl or $C_{6-10}$ aryl; O or S.

Preferred compounds within Formula II also include those compounds where $A_1$ is an optionally substituted aryl group selected from the group consisting of phenyl and naphthyl, and $A_2$ is an optionally substituted heteroaryl or aryl group selected from the group consisting of pyridyl, pyrimidinyl, 1,3,5-triazinyl, furanyl, thiophenyl, naphthyl, quinolyl, 3,4-methylenedioxyphenyl, 3,4-ethylenedioxyphenyl, indanyl, tetrahydronaphthyl, biphenylmethyl, triphenylmethyl and quinoxalinyl.

Additional preferred compounds within Formula II also include those compounds where $A_1$ is an optionally substituted aryl group selected from the group consisting of phenyl or naphthyl, and $A_2$ is an optionally substituted carbocycle or heterocycle selected from the group consisting of cyclopentyl, cyclohexyl, cycloheptyl, piperidinyl, morpholinyl, pyrrolidinyl, tetrahydrofuranyl, tetrahydropyranyl, cyclohexenyl, adamantyl, exo-norbornyl and cyclopentenyl.

Additional preferred compounds within Formula II include those compounds where $A_1$, is an optionally substituted heteroaryl or aryl group selected from the group consisting of pyridyl, pyrimidinyl, 1,3,5-triazinyl, naphthyl, quinolyl, furanyl, and thiophenyl, and $A_2$ is an optionally substituted heteroaryl or aryl group selected from the group consisting of phenyl, furanyl, thiophenyl, quinolinyl, 3,4-methylenedioxyphenyl, 3,4-ethylenedioxyphenyl, indanyl, tetrahydronaphthyl and naphthyl.

Additional preferred compounds within Formula II include those compounds where $A_1$ is an optionally substituted. saturated or partially unsaturated carbocycle or heterocycle selected from the group consisting of cyclopentyl, cyclohexyl, cycloheptyl, morpholinyl, piperidinyl, pyrrolidinyl, tetrahydrofuranyl and tetrahydropyranyl, and $A_2$ is an optionally substituted aryl or heteroaryl group selected from the group consisting of phenyl, furanyl, thiophenyl, quinolinyl, 3,4-methylenedioxyphenyl, 3,4-ethylenedioxyphenyl, indanyl, tetrahydronaphthyl, or naphthyl.

Exemplary preferred compounds that may be employed in this method of invention include, without limitation:

2-(4-(2-fluorobenzyloxy)benzylamino)-2-methyl-propanamide;

2-(4-(4-fluorophenoxy)benzylamino)-2-methyl-propanamide;

2-(4-(3,4-methylenedioxyphenoxy)benzylamino)-2-methyl-propanamide;

2-(4-(3,4-methylenedioxybenzyloxy)benzylamino)-2-methyl-propanamide;

2-(4-cyclohexyloxybenzylamino)-2-methyl-propanamide;

2-(4-(5,6,7,8-tetrahydro-2-naphthoxy)benzylamino)-2-methyl-propanamide;

2-(4-(2-adamantanoxy)benzylamino)-2-methyl-propanamide;

2-(4-(4-Chloro-2-fluorophenoxy)benzylamino)-2-methyl-propanamide;

2-(4-(2,4-difluorophenoxy)benzylamino)-2-methyl-propanamide;

2-(4-(3,4-difluorophenoxy)benzylamino)-2-methyl-propanamide;

2-(4-(6-bromo-4-fluorophenoxy)benzylamino)-2-methyl-propanamide;

2-(4-(4-nitrophenoxy)benzylamino)-2-methyl-propanamide;

2-(4-(4-tetrahydropyranoxy)benzylamino)-2-methyl-propanamide;

2-(4-(3,5-difluorophenoxy)benzylamino)-2-methyl-propanamide;

2-(4-(4-chlorophenoxy)benzylamino)-2-methyl-propanamide;

2-(4-(4-methylphenoxy)benzylamino)-2-methyl-propanamide;

2-(4-(2-chloro-4-fluorophenoxy)benzylamino)-2-methyl-propanamide;

2-(4-(5-indanoxy)benzylamino)-2-methyl-propanamide;

2-(4-cycloheptoxybenzylamino)-2-methyl-propanamide;

2-(4-(1-methyl4-piperidinoxy)benzylamino)-2-methyl-propanamide;

2-(4-(exo-2-norbornoxy)benzylamino)-2-methyl-propanamide;
2-(3-(4-fluorophenoxy)-5-pyridylmethylamino)-2-methyl-propanamide;
2-(4-(4-pyridinoxy)benzylamino)-2-methyl-propanamide;
2-(3-fluoro-4-(4-fluorophenyl)benzylamino)-2-methyl-propanamide;
2-(4-(2-pyrimidinoxy)benzylamino)-2-methyl-propanamide;
2-(4-(6-quinolinoxy)benzylamino)-2-methyl-propanamide;
2-(4-(N. N-diphenylamino)benzylamino)-2-methyl-propanamide;
2-(4-diphenylmethoxy)benzylamino-2-methyl-propanamide; and
2-(4-triphenylmethoxy)benzylamino-2-methyl-propanamide.

Since the compounds of Formula I and II are blockers of sodium (Na$^+$) channels. a number of diseases and conditions mediated by sodium ion influx can be treated employing these compounds. Therefore, the invention is related to a method of treating, preventing or ameliorating neuronal loss associated with stroke, global and focal ischemia, CNS trauma, hypoglycemia and surgery, spinal cord trauma; as well as treating or ameliorating neurodegenerative diseases including Alzheimer's disease, amyotrophic lateral sclerosis, Parkinson's disease, treating or ameliorating anxiety, convulsions, glaucoma, migraine headache. and muscle spasm. The compounds of Formula I and II are also useful as antimanic depressants, as local anesthetics, and as antiarrhythmics; as well as for treating, preventing or ameliorating pain including surgical, chronic and neuropathic pain. In each instance, the methods of the present invention require administering to an animal in need of such treatment an effective amount of a sodium channel blocker of the present invention, or a pharmaceutically acceptable salt or prodrug thereof.

The present invention is also directed to novel compounds within the scope of Formula II. These compounds include those compounds of Formula II where:

$R_1$, $R_2$, $R_3$ and $R_4$ are independently hydrogen, alkyl, cycloalkyl, alkenyl, alkynyl, haloalkyl, aryl, aminoalkyl, hydroxyalkyl, alkoxyalkyl or carboxyalkyl;

$R_5$, $R_6$ and $R_7$ are independently hydrogen, alkyl, cycloalkyl, alkenyl, alkynyl, haloalkyl, aryl, aminoalkyl, hydroxyalkyl, alkoxyalkyl or carboxyalkyl, or $R_5$, is defined as above, and $R_6$ and $R_7$ together with the nitrogen atom to which they are attached form a heterocycle, including piperidine, piperazine, morpholine;

$A_1$ and $A_2$ are independently aryl, heteroaryl, saturated or partially unsaturated carbocycle or saturated or partially unsaturated heterocycle, any of which is optionally substituted;

X is one or O, S, $NR_8$, $CH_2$, $C(O)$, $NR_8C(O)$, $C(O)NR_8$, SO, $SO_2$ or a covalent bond; where $R_8$ is hydrogen, alkyl, cycloalkyl, alkenyl, alkynyl, haloalkyl, aryl, aminoalkyl, hydroxyalkyl, alkoxyalkyl or carboxyalkyl;

n is 0, 1, 2 or 3. provided that:

when X is O, S, $CH_2$ or NH; $R_1$ and $R_2$ are hydrogen, $R_3$ and $R_4$ are methyl or ethyl, then $A_1$ and $A_2$ are not both phenyl.

Specifically, preferred substituted 2-aminoacetamides are represented by Formulae III–VIII. In particular. a preferred embodiment is represented by Formulae III and IV:

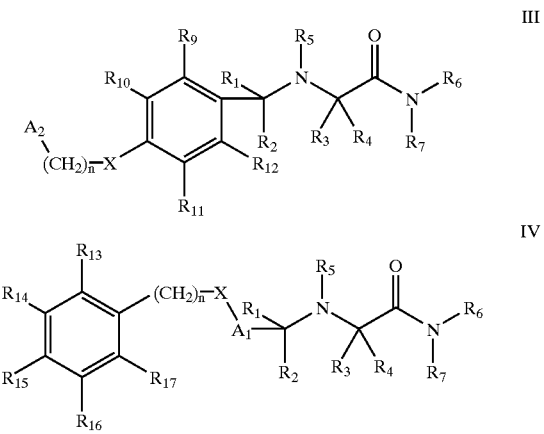

or a pharmaceutically acceptable salt or prodrug thereof, wherein $R_1$, $R_2$, $R_3$, $R_4$, $R_5$, $R_6$, $R_7$, X, n, $A_1$, and $A_2$ are as defined previously with respect to Formula II; and $R_9$, $R_{10}$, $R_{11}$, and $R_{12}$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano. acylamido, hydroxy, thiol, acyloxy, azido, alkoxy, carboxy, carbonylamido or alkylthiol; or $R_9$ and $R_{10}$ or $R_{11}$ and $R_{12}$ are taken together with the carbon atoms to which they are attached to form a carbocycle or heterocycle. Examples of bridges formed by $R_9$ and $R_{10}$ or $R_{11}$ and $R_{12}$ taken together are —CH$_2$O—, —OCF$_2$O—, —(CH$_2$)$_3$—, —(CH$_2$)$_4$—, —OCH$_2$CH$_2$O—, —CH$_2$N(R$_{18}$)CH$_2$—, —CH$_2$CH$_2$N(R$_{18}$)CH$_2$—, —CH$_2$N(R$_{18}$)CH$_2$CH$_2$— and —CH=CH—CH=CH—;

where $R_{18}$ is hydrogen, alkyl or cycloalkyl;

provided that when $A_2$ in Formula III is an optionally substituted phenyl, then $R_9$ and $R_{10}$ or $R_{11}$ and $R_{12}$ are taken together with the carbon atoms to which they are attached to form a carbocycle or heterocycle.

$R_{13}$, $R_{14}$, $R_{15}$, $R_{16}$ and $R_{17}$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamido, hydroxy, thiol, acyloxy, azido, alkoxy, carboxy, carbonylamido or alkylthiol; or one of $R_{13}$ and $R_{14}$, or $R_{14}$ and $R_{15}$, or $R_{15}$ and $R_{16}$, or $R_{16}$ and $R_{17}$ are taken together with the carbon atoms to which they are attached to form a carbocycle or heterocycle. Examples of bridges formed by $R_{13}$ and $R_{14}$, or $R_{14}$ and $R_{15}$, or $R_{15}$ and $R_{16}$, or $R_{16}$ and $R_{17}$ taken together are —OCH$_2$O—, —OCF$_2$O—, —(CH$_2$)$_3$—, —(CH$_2$)$_4$—, —OCH$_2$CH$_2$O—, —CH$_2$N(R$_{18}$)CH$_2$—, —CH$_2$CH$_2$N(R$_{18}$)CH$_2$—, —CH$_2$N(R$_{18}$)CH$_2$CH$_2$— and —CH=CH—CH=CH—;

where $R_{18}$ is hydrogen, alkyl or cycloalkyl.

provided that when $A_1$ in Formula IV is an optionally substituted phenyl, then $R_{13}$ and $R_{14}$, or $R_{14}$ and $R_{15}$, or $R_{16}$, and $R_{16}$, or $R_{16}$ and $R_{17}$ are taken together with the carbon atoms to which they are attached to form a carbocycle or heterocycle.

Preferred values of $A_2$ in Formula III include furanyl, thiophenyl, quinolinyl, 3,4-methylenedioxyphenyl, 3,4-ethylenedioxyphenyl, indanyl, tetrahydronaphthyl, and naphthyl.

Preferred values of $A_1$ in Formula IV include furanyl, thiophenyl, quinolinyl, 3,4-methylenedioxyphenyl, 3,4-ethylenedioxyphenyl, indanyl, tetrahydronaphthyl and naphthyl.

Another preferred embodiment of the invention includes substituted 2-aminoacetamides represented by Formula V and Formula VI:

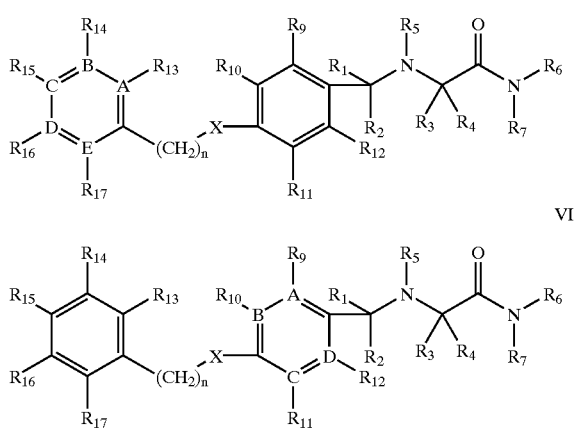

or a pharmaceutically acceptable salt or prodrug thereof, wherein $R_1$–$R_7$, $R_9$–$R_{12}$, $R_{13}$–$R_{17}$, n and X are as defined previously with respect to Formulae II, III and IV; and A, B, C, D and E are independently nitrogen or carbon, provided that no more than three of A, B, C, D and E are nitrogen, and there is no substituent. except for oxygen (when the nitrogen is present as a N-oxide), present on A, B, C, D or E when said A, B, C, D or E represents nitrogen.

Preferred compounds of Formula V are those where one, two or three of A through E are nitrogens. Preferred compounds of Formula VI are those where one or two of A through D are nitrogens.

Another preferred embodiment of the invention includes substituted 2-aminoacetamide represented by Formula VII and Formula VIII:

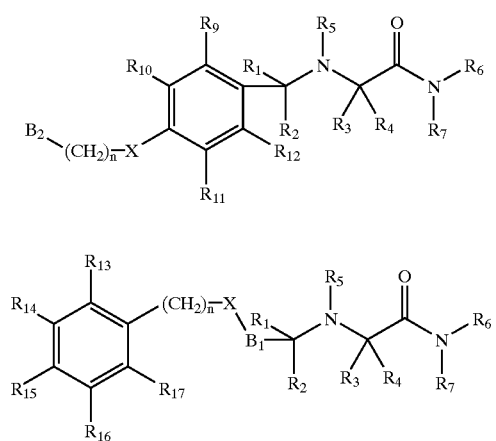

or a pharmaceutically acceptable salt or prodrug thereof, wherein $R_1$–$R_7$, $R_9$–$R_{12}$, $R_{13}$–$R_{17}$, n and X are as defined previously with respect to Formulae II, III and IV; and $B_1$ is an optionally substituted, saturated or partially unsaturated carbocycle or optionally substituted, saturated or partially unsaturated heterocycle; and $B_2$ is an optionally substituted, saturated or partially unsaturated carbocycle or optionally substituted, saturated or partially unsaturated heterocycle.

Preferred $B_1$ and $B_2$, independently include cyclopentyl, cyclohexyl, cycloheptyl, tetrahydrofuranyl, tetrahydropyranyl, pyrrolidinyl and piperidinyl.

Generally, preferred compounds of Formulae II–VIII are those compounds where $R_1$ and $R_2$ is hydrogen or alky, more preferably hydrogen, methyl or ethyl, and where $R_3$ and $R_4$ are independently hydrogen or $C_{1-4}$ alkyl.

Preferred values of X in Formulae II–VIII are O and S.

Preferred values of $R_5$–$R_7$ with respect to Formulae II–VIII are hydrogen or $C_{1-4}$ alkyl.

Preferred values of $R_9$–$R_{12}$, and $R_{13}$–$R_{17}$, with respect to Formulae II–VIII include hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamido, hydroxy, thiol, $C_1$–$C_6$ acyloxy. azido, $C_1$–$C_6$ alkoxy, and carboxy. Alternatively, $R_9$ and $R_{10}$ or $R_{11}$ and $R_{12}$, or two adjacent $R_{13}$ through $R_{17}$ can form a bridge selected from the group consisting of —$OCH_2O$—, —$CH_2$)—, —$(CH_2)_4$—, —$OCH_2CH_2O$—, —$CH_2N(R_{18})CH_2$—, —$CH_2CH_2N(R_{18})CH_2$—, —$CH_2N(R_{18})CH_2CH_2$—, and —CH=CH—CH=CH—, where $R_{18}$ is hydrogen or $C_1$–$C_6$ alkyl. Most preferably, at least one, two or three of $R_9$, $R_{10}$, $R_{11}$, $R_{12}$ are hydrogen. Most preferably, at least one, two or three of $R_{13}$ through $R_{17}$ are hydrogen.

With respect to the novel methods of treatment of the present invention, an additional preferred subset of substituted 2-aminoacetamide compounds includes compounds of Formula II, wherein $A_1$ and $A_2$ are phenyl moieties, that $A_2$ is substituted by one or two substituents independently selected from the group consisting of hydrogen, $C_{1-6}$ alkyl, halogen, hydroxy, $C_{1-6}$ alkoxy, or trifluoromethyl; each of $R_1$ and $R_2$ are hydrogen; $R_3$ and $R_4$ are methyl; and $R_5$–$R_7$ are independently $C_{1-6}$ alkyl or $C_{3-7}$ cycloalkyl.

Useful compounds in this aspect of the present invention include:

2-(4-(2-fluorobenzyloxy)benzylamino)-2-methyl-propanamide;

2-(4-(4-fluorophenoxy)benzylamino)-2-methyl-propanamide;

2-(4-(3,4-methylenedioxyphenoxy)benzylamino)-2-methyl-propanamide;

2-(4-(3,4-methylenedioxybenzyloxy)benzylamino)-2-methyl-propanamide;

2-(4-cyclohexyloxybenzylamino)-2-methyl-propanamide;

2-(4-(5,6,7,8-tetrahydro-2-naphthoxy)benzylamino)-2-methyl-propanamide;

2-(4-(2-adamantanoxy)benzylamino)-2-methyl-propanamide;

2-(4-(4-Chloro-2-fluorophenoxy)benzylamino)-2-methyl-propanamide;

2-(4-(2,4-difluorophenoxy)benzylamino)-2-methyl-propanamide;

2-(4-(3,4-difluorophenoxy)benzylamino)-2-methyl-propanamide;

2-(4-(6-bromo-4-fluorophenoxy)benzylamino)-2-methyl-propanamide;

2-(4-(4-nitrophenoxy)benzylamino)-2-methyl-propanamide;

2-(4-(4-tetrahydropyranoxy)benzylamino)-2-methyl-propanamide;

2-(4-(3 ,5-difluorophenoxy)benzylamino)-2-methyl-propanamide;

2-(4-(4-chlorophenoxy)benzylamino)-2-methyl-propanamide;
2-(4-(4-methylphenoxy)benzylamino)-2-methyl-propanamide;
2-(4-(2-chloro-4-fluorophenoxy)benzylamino)-2-methyl-propanamide;
2-(4-(5-indanoxy)benzylamino)-2-methyl-propanamide;
2-(4-cycloheptoxybenzylamino)-2-methyl-propanamide;
2-(4-(1-methyl4-piperidinoxy)benzylamino)-2-methyl-propanamide;
2-(4-(exo-2-norbornoxy)benzylamino)-2-methyl-propanamide;
2-(3-(4-fluorophenoxy)-5-pyridylmethylamino)-2-methyl-propanamide;
2-(4-(4-pyridinoxy)benzylamino)-2-methyl-propanamide;
2-(3-fluoro-4-(4-fluorophenyl)benzylamino)-2-methyl-propanamide;
2-(4-(2-pyrimidinoxy)benzylamino)-2-methyl-propanamide;
2-(4-(6-quinolinoxy)benzylamino)-2-methyl-propanamide;
2-(4-(N,N-diphenylamino)benzylamino)-2-methyl-propanamide;
2-(4-diphenylmethoxy)benzylamino-2-methyl-propanamide: and
2-(4-triphenylmethoxy)benzylamino-2-methyl-propanamide.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

Useful cycloalkyl groups include $C_{3-8}$ cycloalkyl groups. Typical cycloalkyl groups include cyclopropyl, cyclobutyl, cyclopentyl and cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups include $C_{2-6}$ alkenyl groups, preferably $C_{2-4}$ alkenyl. Typical $C_{2-4}$ alkenyl groups include ethenyl, propenyl, isopropenyl, butenyl, and sec.-butenyl.

Useful alkynyl groups include $C_{2-6}$ alkynyl groups, preferably $C_{2-4}$ alkynyl. Typical $C_{2-4}$ alkynyl groups include ethynyl, propynyl, butynyl, and 2-butynyl groups.

Useful arylalkyl groups include any of the above-mentioned $C_{1-10}$ alkyl groups substituted by any of the above-mentioned $C_{6-14}$ aryl groups. Typical groups include benzyl, phenethyl and naphthylmethyl.

Useful arylalkenyl groups include any of the above-mentioned $C_{2-4}$ alkenyl groups substituted by any of the above-mentioned $C_{6-14}$ aryl groups.

Useful arylalkynyl groups include any of the above-mentioned $C_{2-4}$ alkynyl groups substituted by any of the above-mentioned $C_{6-14}$ aryl groups. Typical groups include phenylethynyl and phenylpropynyl.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulphur substituted by one of the $C_{1-10}$ alkyl groups mentioned above.

Useful acylamino groups are any $C_{1-6}$ acyl (alkanoyl) attached to an amino nitrogen, e.g. acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl and pyrazolinyl groups.

Useful heterocycloalkyl groups include any of the above-mentioned $C_{1-10}$ alkyl groups substituted by any of the above-mentioned heterocyclic groups.

Useful heteroaryl groups include any one of the following: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbazolyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, 4-nitrobenzofurazan, benzimidazolyl, 2-okindolyl and 2-oxobenzimidazolyl. Where the heteroaryl group contains a nitrogen atom in a ring, such nitrogen atom may be in the form of an N-oxide, e.g. a pyridyl N-oxide. pyrazinyl N-oxide, pyrimidinyl N-oxide and the like.

Useful heteroarylalkyl groups include any of the above-mentioned $C_{1-10}$ alkyl groups substituted by any of the above-mentioned heteroaryl groups.

Useful heteroarylalkenyl groups include any of the above-mentioned $C_{2-4}$ alkenyl groups substituted by any of the above-mentioned heteroaryl groups.

Useful heteroarylalkynyl groups include any of the above-mentioned $C_{2-4}$ alkynyl groups substituted by any of the above-mentioned heteroaryl groups.

Useful amino groups include —$NH_2$, —$NHR_{19}$, and —$NR_{19}R_{20}$, wherein $R_{19}$ and $R_{20}$ are $C_{1-10}$ alkyl or cycloalkyl groups as defined above.

Useful aminocarbonyl groups are carbonyl groups substituted by —$NH_2$, —$NHR_{19}$, and —$NR_{19}R_{20}$, wherein $R_{19}$ and $R_{20}$ are $C_{1-10}$ alkyl groups.

Optional substituents on any of the aryl, heterocyclic, heteroaryl, and cycloalkyl rings in Formulae II–VIII include any one of halo, haloalkyl, aryl, heterocycle, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro. amino, ureido, cyano, acylamino, hydroxy, thiol, acyloxy, azido, alkoxy, carboxy, aminocarbonyl, and alkylthiol groups mentioned above. Preferred optional substituents include: halo, haloalkyl, hydroxyalkyl, aminoalkyl, nitro, alkyl, alkoxy and amino.

Certain of the compounds of Formula II may exist as optical isomers and the invention includes both the racemic mixtures of such optical isomers as well as the individual entantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate acetic acid, dichloroacetic acid and oxalate.

Examples of prodrugs include esters or amides of Formula II with $R_1$–$R_7$ as hydroxyalkyl or aminoalkyl, and these may be prepared by reacting such compounds with anhydrides such as succinic anhydride.

The invention is also directed to a method for treating disorders responsive to the blockade of sodium channels in animals suffering thereof. Particular preferred embodiments of the substituted 2-aminoacetamide for use in method of this invention are represented by previously defined Formula II.

The compounds of this invention may be prepared using methods known to those skilled in the art, or by the novel methods of this invention. The methods described in PCT published application WO97/05102, can be employed to synthesize compounds within the scope of the invention.

Compounds with Formulae II–VIII can be prepared as illustrated by exemplary reactions in Schemes 1–5.

Scheme 1

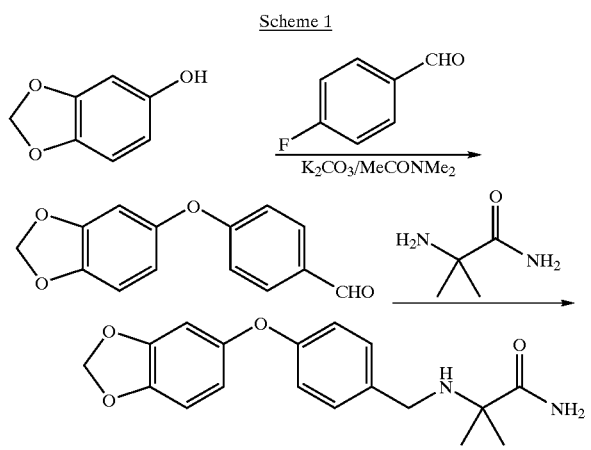

Scheme 2

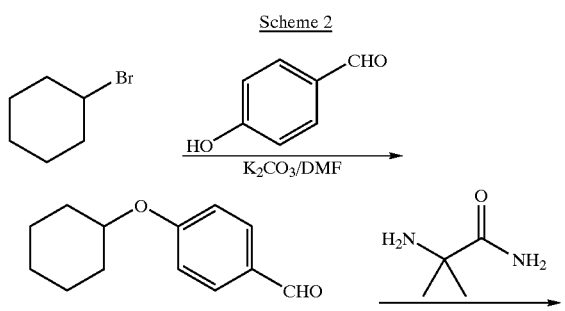

-continued

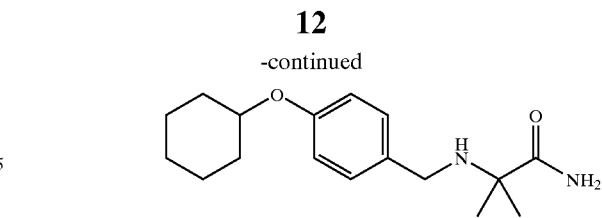

Scheme 3

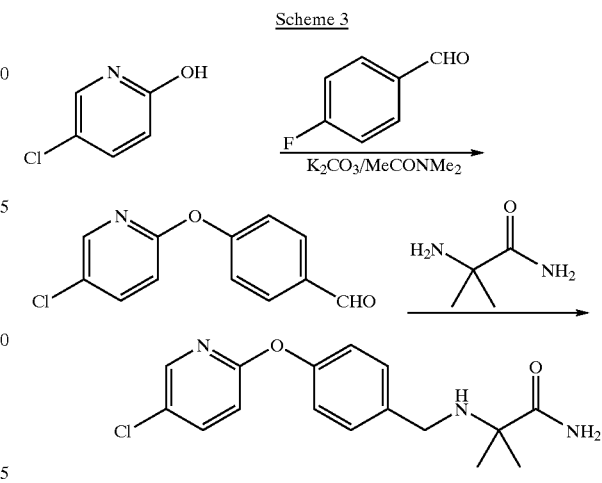

Scheme 4

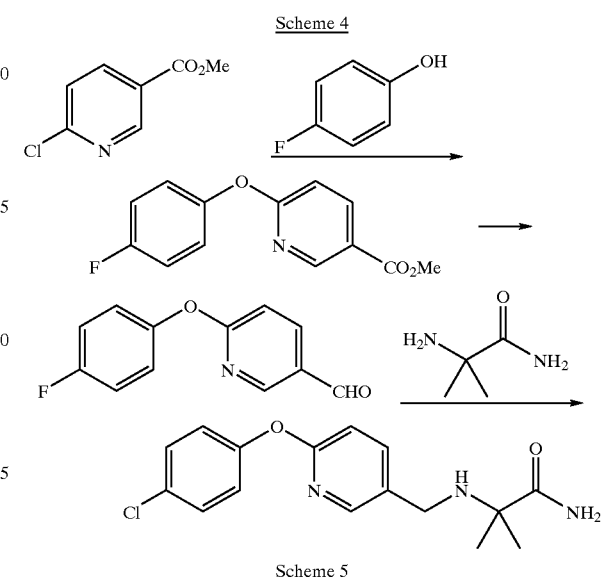

Scheme 5

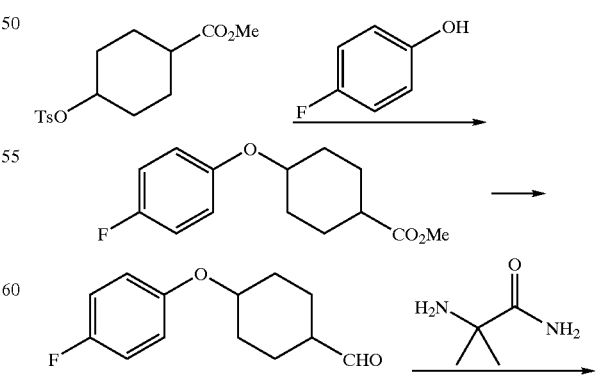

-continued

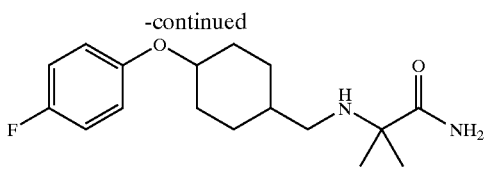

The compounds of the present invention were assessed by electrophysiological assays in dissociated hippocampal neurons for sodium channel blocker activity. These compounds also could be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of Na$^+$ permeability in response to depolarization associated with the action potential in many excitable cells including muscle, nerve and cardiac cells.

One aspect of the present invention is the discovery of the mechanism of action of the compounds herein described as specific Na$^+$ channel blockers. In one aspect of the present invention it has been discovered that compounds disclosed in international published application WO 97/05102 are specific Na$^+$ channel blockers. Based upon the discovery of this mechanism, these compounds, as well as novel compounds described herein, are contemplated to be useful in treating or preventing neuronal loss due to focal or global ischemia, and in treating or preventing neurodegenerative disorders including ALS, anxiety, and epilepsy. They are also expected to be effective in treating, preventing or ameliorating neuropathic pain, surgical pain and chronic pain. The compounds are also expected to be useful as antiarrhythmics, anesthetics and antimanic depressants.

The present invention is directed to compounds of Formulae II that are blockers of voltage-sensitive sodium channels. According to the present invention, those compounds having preferred sodium channel blocking properties exhibit an IC$_{50}$ of about 100 μM or less in the electrophysiological assay described herein. Preferably, the compounds of the present invention exhibit an IC$_{50}$ of 10 μM or less. Most preferably, the compounds of the present invention exhibit an IC$_{50}$ of about 1.0 μM or less. Substituted 2-aminoacetamide disclosed in WO 97/05102, as well as novel compounds of the present invention, may be tested for their Na$^+$ channel blocking activity by the following electrophysiological and binding assays.

Electrophysiological Assay

Cell preparation: Acute cultures of rat hippocampal neurons were prepared daily using a modification of procedures described previously (Kuo and Bean, Mol. Pharm. 46:716–725 (1994)). Briefly, hippocampi were isolated from 3–11 day old rat pup brains (Sprague-Dawley; Charles River) and were sectioned, by hand, into 0.5–1 mm thick transverse slices (Whittemore and Koerner, Eur. J. Pharm. 192:435–438 (1991)). Slices were incubated for at least- 30 min at room temperature (20–24° C.) in an oxygenated medium (124 mM NaCl, 3.3 mM KCl. 2.4 mM MgSO$_4$, 2.5 mM CaCl$_2$, 1.2 mM KH$_2$PO$_4$, 26 mM NaHCO$_3$, pH=7.4) continuously bubbled with 5% CO$_2$/95% O$_2$. Prior to recording, 4–5 slices were transferred to an oxygenated dissociation medium (82 mM NaSO$_4$, 30 mM K$_2$SO$_4$, 3 mM MgCl$_2$, 2 mM HEPES, 26 mM NaHCO$_3$, 0.001% phenol red, pH=7.4) containing 3 mg/mL protease XXIII (Sigma, St. Louis, Mo.) and incubated for 10–15 min at 37° C., while continuously bubbling with 5% CO$_2$/95% O$_2$. Enzymatic digestion was terminated by transferring the slices to dissociation medium without bicarbonate, supplemented with 1 mg/mL bovine serum albumin and 1 mg/mL trypsin inhibitor (Sigma, St. Louis, Mo.). Slices were then transferred to a 35 mm culture dish containing dissociation medium without bicarbonate, and triturized with a fire-polished glass Pasteur pipette to release single cells. Cells were allowed to settle in this dish for ~30 minutes and were then used for making electrical recordings.

Patch-clamp recordings of voltage-sensitive Na$^+$ currents: Whole-cell voltage-clamp recordings were made using conventional patch-clamp technique (Hamill et al., Pfluegers Arch. 391:85–100 (1981)) with an Axopatch 200A amplifier (Axon Instruments, Foster City, Calif.). Recordings were made within 2–3 hours after neuron dissociation. The recording chamber was continuously superfused with Tyrode's solution (156 mM NaCl, 3.5 mM KCl, 2 mM CaCl$_2$, 5 mM NaHCO$_3$, 10 mM HEPES, 10 mM glucose. pH 7.4) at a speed of about 1 ml/min. Thin-walled pipettes were pulled from 100-μl Clay Adams Accu-Fill 90 Micropet disposable pipettes (Becton, Dickenson and Company, Parsipanny, N.J.), fire-polished and sylgarded (Dow-Corning, Midland, Mich.). The pipette resistances ranged from 1 to 3 MΩ when the pipettes were filled with internal solution containing (in mM): 130 CsF, 20 NaCl, 1 CaCl$_2$, 2 MgCl$_2$, 10 EGTA, 10 HEPES, pH adjusted to 7.4 with CsOH. Drugs and intervening wash-outs were applied through a linear array of flow pipes (Drummond Microcaps, 2-μl, 64-mm length). Compounds are dissolved in dimethylsulfoxide (DMSO) to make a 10 mM stock solution, which was subsequently diluted into Tyrode's solution to give final concentrations of 0.1–20 μM.- At the highest (1%) concentration. DMSO inhibited the size of Na$^+$ current only slightly. Currents were recorded at room temperature (22–25° C.), filtered at 5 kHz with 4-pole Bessel filter, digitized at 20–50-μs intervals, and stored using Digidata 1200 analog/digital interface with Pclamp6/Clampex software (Axon Instruments). Residual series resistance ranged from 0.4 to 0.8 MΩ after partial compensation (typically ~90%). The inhibitory potency of drugs was assessed by measuring reductions in the peak amplitude of Na$^+$ currents induced by increasing concentrations of compounds tested. Na$^+$ currents were elicited by stepping membrane voltage from holding potentials over the range –100 mV to –50 mV, to a pulse potential of –10 mV. The test pulse duration was 5–10 msec, repeated at a frequency ≦1 Hz. Concentration-inhibition curves were fitted with equation 1:

$$I/I_{control}=1/(1+([compound])/IC_{50}))$$ Eq. 1 where $I_{control}$ is the maximal Na$^+$ current in the absence of antagonist, [compound] is the drug concentration, and IC$_{50}$ is the concentration of compound that produces half maximal inhibition.

Binding Assay

The ability of compounds of the present invention to modulate either site 1 or site 2 of the Na$^+$ channel was determined following the procedures fully described in Yasushi. J. Biol. Chem. 261:6149–6152 (1986) and Creveling, Mol. Pharmacol. 23:350–358 (1983), respectively. Rat forebrain membranes were used as sources of Na$^+$ channel proteins. The binding assays were conducted in 130 μM choline chloride at 37° C. for 60-minute incubation with [$^3$H] saxitoxin and [$^3$H] batrachotoxin as radioligands for site 1 and site 2, respectively.

The compounds of the present invention may be tested for in vivo anticonvulsant activity after iv or ip injection using a number of anticonvulsant tests in mice (audiogenic seizure model in DBA-2 mice, pentylenetetrazol-induced seizures in mice, maximum electroshock seizure test (MES)).

The compounds may be tested for their neuroprotective activity after focal and global ischemia produced in rats or gerbils according to the procedures described in Buchan et al. (*Stroke*, Suppl. 148–152 (1993)) and Sheardown et al. (*Eur. J Pharmacol.* 236:347–353 (1993)) and Graham et al. (*J. Pharmacol. Exp. Therap.* 276:1–4 (1996)).

The compounds may be tested for their neuroprotective activity after traumatic spinal cord injury according to the procedures described in Wrathall et. al. (*Exp. Neurology* 137:119–126 (1996)) and Iwasaki et. al. (*J. Neuro Sci.* 134:21–25 (1995)).

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthesia, arrhythmia, manic depression, and pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular 2-aminoacetamide of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the particular 2-aminoacetamide of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered.

Suitable lipophilic solvents or vehicles include fatty oils, for example, sesame oil, or synthetic fatty acid esters, for example, ethyl oleate or triglycerides or polyethylene glycol400 (the compounds are soluble in PEG400). Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

2-(4-(2-Fluorobenzyloxy)benzylamino)-2-methyl-propanamide as Na$^+$ Channel Blocker 2-(4-(2-Fluorobenzyloxy)benzylamino)-2-methyl-propanamide was tested in the electrophysiological and binding assays described above and produced dose-dependent inhibition of voltage-gated Na$^+$ currents recorded in acutely dissociated rat hippocampal neurons. The blocking effect of this compound on Na$^+$ currents was highly sensitive to the holding voltage. For example, at concentrations between 0.1–10 µM, 2-(4-(2-fluorobenzyloxy) benzylamino)-2-methyl-propanamide had very little effect on Na$^+$ currents activated from a holding membrane voltage of –100 mV, but inhibited currents with increasing potency as the holding potential was progressively depolarized. The most potent block in these studies was seen at a membrane holding voltage of –65 mV. The decrease in current was due to steady-state inactivation of the Na$^+$ channels.

This data indicates that 2-(4-(2-fluorobenzyloxy) benzylamino)-2-methyl-propanamide binds to voltage-sensitive Na$^+$ channels in their inactivated states and has weak potency towards Na$^+$ channels in their resting states (Ragsdale et al, *Mol. Pharmacol.* 40:756–765 (1991); Kuo and Bean, *Mol. Pharmacol.* 46:716–725 (1994)). The apparent antagonist dissociation constant ($K_d$) of this compound for inactivated Na$^+$ channels is ~1.2 µM.

EXAMPLE 2

2-(4-(3,4-Methylenedioxyphenoxy)benzylamino)-2-methyl-propanamide a) 4-(3,4-Methylenedioxyphenoxy)benzaldehyde: A mixture of sesamol (5.13 g, 37.1 mmol), 4-fluorobenzaldehyde (4.0 mL, 37.3 mmol), potassium carbonate (6.21 g, 44.9 mmol) in N,N-dimethylacetamide (50 mL) was refluxed for 23 h. The mixture was added to water and extracted with an ethyl acetate/hexane solution. The organic layer was washed with aqueous sodium hydroxide (2 N), dried over sodium sulfate, and evaporated under reduced pressure to give crude product. The crude product was purified by flash chrmoatography to give a pink solid, which was decolorized by refluxing with activated charcoal in chloroform for 1 h. Filtration through Celite and removal of the chloroform in vacuo gave the desired aldehyde. $^1$H NMR (CDCl$_3$) δ9.91 (s, 1H), 7.83 (d, J=9.0 Hz, 2H), 7.03 (d, J=8.4 Hz, 2H), 6.82 (d, J=8.7Hz, 1H), 6.62 (d, J=2.4 Hz, 1H), 6.58–6.54 (m, 1H), 6.02 (s, 2H).

b) 2-Amino-2,2-dimethylethanamide: A solution of HCl in dioxane (4.0 M), methanol (54 ml) and aminoisobutyric acid (11.7 g, 0.114 mol) was refluxed for 6 h. Once at rt, the solution was concentrated to a white solid. NMR of the solid showed that the solid was a mixture of aminoisobutyric acid and methyl 2-amino-2,2-dimethylacetate. This crude intermediate was heated to 50 degree Celsius in aqueous ammonium hydroxide (29%, 140 ml) in a sealed tube for 24 hours. The solution was cooled to room temperature, then evaporated under reduced pressure to give a white solid. $^1$H NMR of the solid showed that the white solid contained 40% of the title product. $^1$H NMR (CDCl$_3$) δ7.80 (s, 2H), 7.48 (s, 2H), 1.27 (s, 6H).

c) 2-(4-(3,4-Methylenedioxyphenoxy)benzylamino)-2-methylpropanamide: To a solution of 4-(3,4-methylenedioxyphenoxy)benzaldehyde (0.51 g, 0.21 mmol) in 30 mL of anhydrous ethanol was added 3 Å molecular sieves (1 g), and 2-amino-2,2-dimethylethanamide (1.67 g, 40% by weight by $^1$H NMR, 0.49 mmol). After stirring for 24 h, the resulting mixture was treated with sodium cyanoborohydride (95%; 1.0 g, 16 mmol). After stirring for an additional 8 h, the reaction was quenched with water. The aqueous layer was extracted three times with an ethyl acetate/hexane mixture. The combined organic layers were dried over sodium sulfate and evaporated under reduced pressure. The crude product was purified by column chromatography to give 77 mg (11%) of the title product, mp=123–124° C. $^1$H NMR (CDCl$_3$) δ7.25 (d, J=8.0 Hz, 2H), 6.92 (d, J=8.4 Hz, 2H), 6.74 (d, J=8.4 Hz, 1H), 6.55 (s, 1H), 6.47 (d, J=8.1 Hz, 1H), 5.96 (s, 2H), 5.47 (bs, 2H), 3.66 (s, 2H), 1.42 (s, 6H).

The following compounds were prepared similarly:
2-(4-(4-Fluorophenoxy)benzylamino)-2-methylpropanamide: mp=103–106° C.; $^1$H NMR (CDCl$_3$) δ7.27 (d, J=8.4 Hz, 2H), 7.02–6.92 (m, 6H), 5.6 (bs, 2H), 3.68 (s, 2H), 1.43 (s, 6H).
2-(4-(2,4-Difluorophenoxy)benzylamino)-2-methylpropanamide: TLC solvent: 60:40 hexane/ethylacetate; TLC Rf 0.5; $^1$H NMR (CDCl$_3$) δ7.27–6.85 (m. 7H), 5.5 (bs, 2H), 3.67 (s, 2H), 1.42 (s, 6H).
2-(4-(5-Indanoxy)benzylamino)-2-methylpropanamide: mp=81–83° C.; $^1$H NMR (CDCl$_3$) δ7.25 (d, J=8.1 Hz, 2H), 7.16 (d, J=8.1 Hz, 1H), 6.95 (d, J=8.4 Hz, 2H), 6.87 (s, 1H), 6.78 (d, J=6.0 Hz, 1H), 5.5 (bs, 2H), 3.66 (s, 2H), 2.88 (t, J=6.9 Hz, 4H), 2.19–2.0 (m, 2H), 1.41 (s, 6H).

The following compounds can be similarly prepared by allowing the appropriate aldehyde precursor to react with 2-methylpropanamide as described above:
2-(4-(3,4-Methylenedioxyphenoxy)benzylamino)-2-methylpropanamide
2-(4-Cyclohexyloxybenzylamino)-2-methylpropanamide
2-(4-(5,6,7,8-tetrahydro-2-naphthoxy)benzylamino)-2-methylpropanamide 2-(4-(2-Adamantanoxy)benzylamino)-2-methylpropanamide
2-(4-(4-Chloro-2-fluorophenoxy)benzylamino)-2-methylpropanamide
2-(4-(2-Chloro-4-fluorophenoxy)benzylamino)-2-methylpropanamide
2-(4-(3,4-Difluorophenoxy)benzylamino)-2-methylpropanamide
2-(4-(3,5-Difluorophenoxy)benzylamino)-2-methylpropanamide
2-(4-(6-Bromo-4-fluorophenoxy)benzylamino)-2-methylpropanamide
2-(4-(4-Nitrophenoxy)benzylamino)-2-methylpropanamide
2-(4-(4-Tetrahydropyranoxy)benzylamino)-2-methylpropanamide
2-(4-(4-Chlorophenoxy)benzylamino)-2-methylpropanamide
2-(4-(4-Methylphenoxy)benzylamino)-2-methylpropanamide
2-(4-Cycloheptoxybenzylamino)-2-methylpropanamide
2-(4-(1-Methyl4-piperidinoxy)benzylamino)-2-methylpropanamide
2-(4-(exo-2-norbornoxy)benzylamino)-2-methylpropanamide
2-(3-(4-Fluorophenoxy)-5-pyridylmethylamino)-2-methylpropanamide
2-(4-(4-Pyridinoxy)benzylamino)-2-methylpropanamide
2-(3-Fluoro-4-(4-fluorophenyl)benzylamino)-2-methylpropanamide
2-(4-(2-Pyrimidinoxy)benzylamino)-2-methylpropanamide
2-(4-(6-Quinolinoxy)benzylamino)-2-methylpropanamide
2-(4-(N,N-diphenylamino)benzylamino)-2-methylpropanamide
2-(4-Diphenylmethoxy)benzylamino)-2-methylpropanamide
2-(4-Triphenylmethoxy)benzylamino)-2-methylpropanamide
2-(4-(3,4-Methylenedioxybenzyloxy)benzylamino)-2-methylpropanamide The ability of selected 2-methylpropanamide derivatives to block maximal electroshock-induced seizures (MES) was determined by the following procedure.

Seizures were induced by application of current (50 mA, 60 pulses/sec, 0.8 msec pulse width, 1 sec duration, D.C.) using a Ugo Basile ECT device (model 7801). Mice were restrained by gripping the loose skin on their dorsal surface and saline-coated corneal electrodes were held lightly against the two cornea. Current was applied and mice were observed for a period of up to 30 sec for the occurrence of a tonic hindlimb extensor response. A tonic seizure was defined as a hindlimb extension in excess of 90 degrees from plane of the body. The 2-methylpropanamides tested were administered iv to mice 10 min before the test procedure.

TABLE 1

Activity of Substituted Benzylamino 2-methylpropanamide in MES iv in mouse

| Substituent | Example No. | iv MES activity (number protected/number screened) |
|---|---|---|
| 4-fluorophenoxy | 2 | 8/8 |
| 3,4-methylenedioxyphenoxy | 2 | 8/8 |
| 2,4-difluorophenoxy | 2 | 8/8 |
| 5-indanoxy | 2 | 1/8 |

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of treating or ameliorating pain in a mammal, comprising administering to a mammal in need of such treatment an effective amount of a compound having the Formula II:

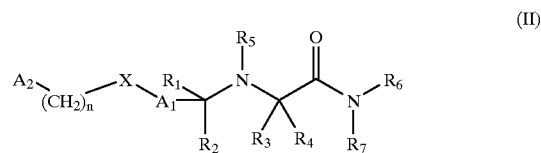

(II)

or a pharmaceutically acceptable salt or prodrug thereof, wherein:

$R_1$, $R_2$, $R_3$ and $R_4$ are independently hydrogen, alkyl, cycloalkyl, alkenyl, alkynyl, haloalkyl, aryl, aminoalkyl, hydroxyalkyl, alkoxyalkyl or carboxyalkyl;

$R_5$, $R_6$ and $R_7$ are independently hydrogen, alkyl, cycloalkyl, alkenyl, alkynyl, haloalkyl, aryl, aminoalkyl, hydroxyalkyl, alkoxyalkyl or carboxyalkyl, or $R_5$, is defined as above, and $R_6$ and $R_7$ together with the nitrogen atom to which they are attached form a heterocycle selected from the group consisting of piperidinyl, piperizinyl, pyrrolidinyl, imidazolidinyl, imidazolinyl, indolinyl, isoindolinyl, morpholinyl, pyrazolidinyl and pyrazolyl;

$A_1$ and $A_2$ are independently aryl, saturated carbocyclic or partially unsaturated carbocyclic, any of which is optionally substituted with any one substituent from the group consisting of halo, haloalkyl, aryl, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, hydroxyalkyl, aminoalkyl, carboxyalkyl, alkoxyalkyl, nitro, amino, ureido, cyano, alkanoylamino, hydroxy, thiol, alkanoyloxy, azido, alkoxy, carboxy, aminocarbonyl, and alkylthiol, wherein optionally substituted heteroaryl is selected from the group consisting of thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbazolyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, 4-nitrobenzofurazan, benzimidazolyl, 2-oxindolyl and 2-oxobenzimidazolyl;

X is one or O, S, $NR_8$, $CH_2$, C(O), $NR_8C(O)$, $C(O)NR_8$, SO, $SO_2$ or a covalent bond; where $R_8$ is hydrogen, alkyl, cycloalkyl, alkenyl, alkynyl, haloalkyl, aryl, aminoalkyl, hydroxyalkyl, alkoxyalkyl or carboxyalkyl; and n is 0, 1, 2 or 3.

2. The method according to claim 1, wherein A₁ nd A₂ are both optionally substituted aryl moieties.

3. The method according to claim 1, wherein:

A₁ and A₂ are phenyl moieties, wherein A₂ is optionally substituted by one or two substituents independently selected from the group consisting of hydrogen, C₁₋₆ alkyl, halogen, hydroxy, C₁₋₄ alkoxy and trifluoromethyl;

R₁ and R₂ are hydrogen;

R₃ and R₄ are methyl;

R₅, R₆ and R₇ are independently hydrogen, C₁₋₆ alkyl, or C₃₋₇ cycloalkyl; and

X is O, S, CH₂, or NH.

4. The method according to claim 1, wherein said compound is selected from the group consisting of:

2-(4-(2-fluorobenzyloxy)benzylamino)-2-methyl-propanamide;

2-(4-(4-fluorophenoxy)benzylamino)-2-methyl-propanamide;

2-(4-cyclohexyloxybenzylamino)-2-methyl-propanamide;

2-(4-(5,6,7,8-tetrahydro-2-naphthoxy)benzylamino)-2-methyl-propanamide;

2-(4-(2-adamantanoxy)benzylamino)-2-methyl-propanamide;

2-(4-(4-chloro-2-fluorophenoxy)benzylamino)-2-methyl-propanamide;

2-(4-(2,4-difluorophenoxy)benzylamino)-2-methyl-propanamide;

2-(4-(3,4-difluorophenoxy)benzylamino)-2-methyl-propanamide;

2-(4-(6-bromo-4-fluorophenoxy)benzylamino)-2-methyl-propanamide;

2-(4-(4-nitrophenoxy)benzylamino)-2-methyl-propanamide;

2-(4-(3,5-difluorophenoxy)benzylamino)-2-methyl-propanamide, 2-(4-(4-chlorophenoxy)benzylamino)-2-methyl-propanamide;

2-(4-(4-methylphenoxy)benzylamino)-2-methyl-propanamide;

2-(4-(2-chloro-4-fluorophenoxy)benzylamino)-2-methyl-propanamide;

2-(4-cycloheptoxybenzylamino)-2-methyl-propanamide;

2-(4-(exo-2-norbornoxy)benzylamino)-2-methyl-propanamide;

2-(3-fluoro-4-(4-fluorophenyl)benzylamino)-2-methyl-propanamide; and 2-(4-(N,N-diphenylamino)benzylamino)-2-methyl-propanamide.

5. A method for treating, preventing or ameliorating pain; providing local anesthesia; or treating arrhythmias, comprising administering to a mammal in need of such treatment an effective amount of a compound having the Formula II:

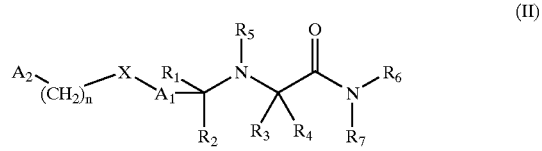

(II)

or a pharmaceutically acceptable salt or prodrug thereof, wherein:

R₁, R₂, R₃ and R₄ are independently hydrogen, alkyl, cycloalkyl, alkenyl, alkynyl, haloalkyl, aryl, aminoalkyl, hydroxyalkyl, alkoxyalkyl or carboxyalkyl;

R₅, R₆ and R₇ are independently hydrogen, alkyl, cycloalkyl, alkenyl, alkynyl, haloalkyl, aryl, aminoalkyl, hydroxyalkyl, alkoxyalkyl or carboxyalkyl, or R₅, is defined as above, and R₆ and R₇ together with the nitrogen atom to which they are attached form a heterocycle selected from the group consisting of piperidinyl, piperizinyl, pyrrolidinyl, imidazolidinyl, imidazolinyl, indolinyl, isoindolinyl, morpholinyl, pyrazolidinyl and pyrazolinyl;

A₁ and A₂ are independently aryl, saturated carbocyclic or partially unsaturated carbocyclic, any of which is optionally substituted with any one substituent from the group consisting of halo, haloalkyl, aryl, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, hydroxyalkyl, aminoalkyl, carboxyalkyl, alkoxyalkyl, nitro, amino, ureido, cyano, alkanoylamino, hydroxy, thiol, alkanoyloxy, azido, alkoxy, carboxy, aminocarbonyl, and alkylthiol, wherein optionally substituted heteroaryl is selected from the group consisting of thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbazolyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, 4-nitrobenzofurazan, benzimidazolyl, 2-oxindolyl and 2-oxobenzimidazolyl;

X is one or O, S, NR₈, CH₂, C(O), NR₈C(O), C(O)NR₈, SO, SO₂ or a covalent bond; where R₈ is hydrogen, alkyl, cycloalkyl, alkenyl, alkynyl, haloalkyl, aryl, aminoalkyl, hydroxyalkyl, alkoxyalkyl or carboxyalkyl; and n is 0, 1, 2 or 3;

provided that when X is O, S, CH₂ or NH; R₁ and R₂ are hydrogen, R₃ and R₄ are methyl or ethyl, then at least one of A₁ and A₂ is other than unsubstituted or substituted phenyl.

6. The method according to claim 5, wherein said method is for treating, preventing or ameliorating pain and said pain is one of neuropathic pain, surgical pain or chronic pain.

7. The method according to claim 6, wherein:

A₁ and A₂ are phenyl moieties, wherein A₁ is substituted by one or two substituents independently selected from the group consisting of hydrogen, $C_{1-6}$ alkyl, halogen, hydroxy, $C_{1-4}$ alkoxy and trifluoromethyl;

$R_1$ and $R_2$ are hydrogen;

$R_3$ and $R_4$ are methyl;

$R_5$, $R_6$ and $R_7$ are independently hydrogen, $C_{1-6}$ alkyl, or $C_{3-7}$ cycloalkyl; and X is O, S, $CH_2$, or NH.

8. The method of claim 5, wherein:

$A_1$ is an optionally substituted aryl group selected from the group consisting of phenyl and naphthyl, and $A_2$ is optionally substituted and selected from the group consisting of naphthyl, 3,4-methylenedioxyphenyl, 3,4-ethylenedioxyphenyl and tetrahydronaphthyl.

9. The method of claim 5, wherein:

$A_1$ is an optionally substituted aryl group selected from the group consisting of phenyl and naphthyl, and $A_2$ is an optionally substituted carbocycle selected from the group consisting of cyclopentyl, cyclohexyl, cycloheptyl, cyclohexenyl, adamantyl, exo-norbonyl and cyclopentenyl.

10. The method of claim 1, wherein each of $R_1$–$R_7$ is independently selected from the group consisting of hydrogen, alkyl and cycloalkyl.

11. The method of claim 10, wherein each of $R_1$ and $R_2$ is hydrogen; each of $R_3$ and $R_4$ is methyl; and each of $R_5$–$R_7$ is independently selected from the group consisting of $C_{1-6}$ alkyl and $C_{3-7}$ cycloalkyl.

12. A method of treating or ameliorating pain in a mammal, comprising administering to a mammal in need of such treatment an effective amount of a compound selected from the group consisting of:

2-(4-diphenylmethoxy)benzylamino-2-methyl-propanamide; and 2-(4-triphenylmethoxy)benzylamino-2-methyl-propanamide.

13. The method of claim 5, wherein each of $R_1$–$R_7$ is independently selected from the group consisting of hydrogen, alkyl and cycloalkyl.

14. The method of claim 13, wherein each of $R_1$ and $R_2$ is hydrogen; each of $R_3$ and $R_4$ is methyl; and each of $R_5$–$R_7$ is independently selected from the group consisting of $C_{1-6}$ alkyl and $C_{3-7}$ cycloalkyl.

15. The method of claim 5, wherein said compound is selected from the group consisting of:

2-(4-cyclohexyloxybenzylamino)-2-methyl-propanamide;

2-(4-(5,6,7,8-tetrahydro-2-naphthoxy)benzylamino)-2-methyl-propanamide;

2-(4-(2-adamantanoxy)benzylamino)-2-methyl-propanamide;

2-(4-cycloheptoxybenzylamino)-2-methyl-propanamide; and 2-(4-(exo-2-norbornoxy)benzylamino)-2-methyl-propanamide.

16. The method of claim 5, wherein said compound is 2-(3-fluoro-4-(4-fluorophenyl)benzylamino)-2-methyl-propanamide.

17. The method of claim 5, wherein said compound is 2-(4-(N,N-diphenylamino)benzylamino)-2-methyl-propanamide.

18. A method for treating, preventing or ameliorating pain; providing local anesthesia; or treating arrhythmias, comprising administering to a mammal in need of such treatment an effective amount of a compound selected from the group consisting of:

2-(4-diphenylmethoxy)benzylamino-2-methyl-propanamide; and 2-(4-triphenylmethoxy)benzylamino-2-methyl-propanamide.

19. A method for treating, preventing or ameliorating pain; providing local anesthesia; or treating arrhythmias, comprising administering to a mammal in need of such treatment an effective amount of a compound selected from the group consisting of:

2-(4-(3,4-methylenedioxyphenoxy)benzylamino)-2-methyl-propanamide; and 2-(4-(3,4-methylenedioxybenzyloxy)benzylamino)-2-methyl-propanamide.

* * * * *

US006479484C1

(12) EX PARTE REEXAMINATION CERTIFICATE (6075th)
United States Patent
Lan et al.

(10) Number: US 6,479,484 C1
(45) Certificate Issued: Jan. 1, 2008

(54) SUBSTITUTED 2-AMINOACETAMIDES AND THE USE THEREOF

(75) Inventors: Nancy C. Lan, South Pasadena, CA (US); Yan Wang, San Diego, CA (US); Sui Xiong Cai, San Diego, CA (US)

(73) Assignee: Euro-Celtique S.A., Luxembourg (LU)

Reexamination Request:
No. 90/006,692, Jul. 2, 2003

Reexamination Certificate for:
Patent No.: 6,479,484
Issued: Nov. 12, 2002
Appl. No.: 09/554,739
Filed: Aug. 8, 2000

(22) PCT Filed: Nov. 20, 1998

(86) PCT No.: PCT/US98/24965
§ 371 (c)(1),
(2), (4) Date: Aug. 8, 2000

(87) PCT Pub. No.: WO99/26614
PCT Pub. Date: Jun. 3, 1999

Related U.S. Application Data
(60) Provisional application No. 60/066,707, filed on Nov. 21, 1997.

(51) Int. Cl.
A61P 29/00 (2006.01)

(52) U.S. Cl. .................... 514/231.2; 514/234.8; 514/249; 514/252.02; 514/256; 514/258.1; 514/259.4; 514/617; 514/618; 514/620; 514/621; 514/622

(58) Field of Classification Search .............. 514/234.8, 514/249, 252.02, 256, 258.1, 259.4, 617, 514/618, 620, 621, 622
See application file for complete search history.

(56) References Cited

U.S. PATENT DOCUMENTS

| | | | |
|---|---|---|---|
| 3,576,864 | A | 4/1971 | Kuppuswamy |
| 4,725,608 | A | 2/1988 | Nakaguchi et al. |
| 5,236,957 | A | 8/1993 | Dostert et al. |
| 5,446,066 | A | 8/1995 | Varasi et al. |
| 5,449,692 | A | 9/1995 | Varasi et al. |
| 5,741,818 | A | 4/1998 | Dimmock |
| 5,945,454 | A | 8/1999 | Pevarello et al. |

FOREIGN PATENT DOCUMENTS

| | | |
|---|---|---|
| WO | WO 91/14334 | 11/1990 |
| WO | WO 96/40628 | 12/1996 |
| WO | WO 9705102 | 2/1997 |
| WO | WO 98/19998 | 5/1998 |
| WO | WO 98/47869 | 10/1998 |
| WO | WO 99/39712 | 8/1999 |

OTHER PUBLICATIONS

Reinauer et al. (Laboratory Diagnosis and Monitoring of Diabetes Mellitus, World Health Organization (2002).*
Ikeda et al. (Arneimittel–Forshung Drug research, 40 (1) pp. 156–162 (1990).*
Kemnitz et al. (Pioglitazone Reduces Insulin Levels and Blood Pressure in Obese Rhesus Monkeys, Third International Symp., Hypertention Associated with Diabetes Mellitus, 1991).*
Bodkin et al. (Am. J. of Phys., Endocrinology and Metabolism, 19 (5): pp. E676–E691 (1989)).*
Anonymous, "Neurogen licenses National Institutes of Health (NIH) anticonvulsants," *SCRIP World Pharmaceutical News 1773*:14, PJB Publications Ltd. (1992).
Anonymous, "Cambridge NeuroScience's grant for channel blockers," *SCRIP World Pharmaceutical News 1870*:8, PJB Publications Ltd. (1993).
Bensimon, G., et al. "A Controlled Trial of Riluzole in Amyotrophic Lateral Sclerosis," *New Engl. J. Med. 330*:585–591, Massachusetts Medical Society (1994).
Brown, C.M. et al., "Neuroprotective properties of lifarizine compared with those of other agents in a mouse model of focal cerebral ischaemia," *British J. Pharmacol, 115*:1425–1432, Stockton Press (1995).
Catterall. W.A., "Common modes of drug action on Na+ channels: local anesthetics, antiarrhythmics and anticonvulsants," *Trends Pharmacol. Sci. 8*:57–65, Elsevier Science Publishers B.V. (1987).
Catterall, W.A., "Neurotoxins That Act on Voltage–Sensitive Sodium Channels in Excitable Membranes,"*Ann. Rev. Pharmacol. Toxicol. 20*:15–43, Annual Reviews Inc. (1980).
Catterall, W.A., "Structure and Function of Voltage–Sensitive Ion Channels," *Science 242*:50–61, American Association for the Advancement of Science (1998).

(Continued)

Primary Examiner—Bruck Kifle

(57) ABSTRACT

The invention is directed to substituted 2-aminoacetamides represented by formula (II):

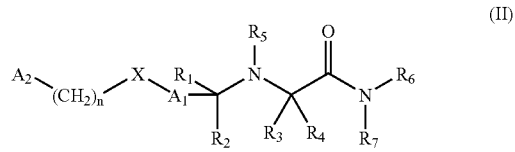

(II)

and to pharmaceutically acceptable salts and prodrugs thereof, wherein the substituents are defined herein. The invention is also directed to the use of substituted 2-aminoacetamides in methods for the treatment of neuronal damage following global and focal ischemia, and for the treatment, prevention or amelioration of pain, as anticonvulsants, as antimanic depressants, as local anesthetics, as antiarrhythmics and for the treatment or prevention of diabetic neuropathy.

OTHER PUBLICATIONS

Denicoff, K.D., et al., "Efficacy of Carbamazepine Compared with Other Agents: A Clinical Practice Survey," *J. Clin. Psychiatry 55*:70–76, Physicians Postgraduate Press (1994).

Dimmock, J.R. et al., "(Aryloxy)aryl Semicarbazones and Related Compounds: A Novel Class of Anticonvulsant Agents Possessing High Activity in the Maximal Electroshock Screen," *J. Med. Chem. 39*:3984–3997, American Chemical Society (1996).

Graham, S.H., et al., "Neuroprotective Effects of a Use–Dependent Blocker of Voltage–Dependent Sodium Channels, BW619C89, in Rat Middle Cerebral Artery Occlusion," *J. Pharmacol. Exp. Ther. 269*:854:–859, The American Society for Pahrmacology and Experimental Therapeutics (1994).

Pevarello, P., et al., "Synthesis and Anticonvulsant Activity of a New Class of 2–[Arylalky)amino]alkanamide Derivatives," *J. Med. Chem. 41*:579–590, American Chemical Society (1998).

Stys, P.K. et al.,"Ionic Mechanism of Anoxic Injury in Mammalian CNS White Matter: Role of $Na^+$ Channels and $Na^+$—$Ca^{2+}$ Exchanger," *J. Neurosci. 12*:430–439, Society for Neuroscience (1992).

Taylor, C.P. and Meldrum, B.S., "$Na^+$ channels as targets for neuroprotective drugs," *Trends Pharmacol. Sci. 16*:309–316, Elsevier (1995).

International Search Report for International Application No. PCT/US98/24965, mailed Mar. 1999.

* cited by examiner

US 6,479,484 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, line 51:

Preferred compounds falling within the scope of Formula II include compounds wherein $A_1$ and $A_2$ are both aryl moieties, preferably both phenyl moieties, that are each optionally independently substituted by one or two substituents independently selected from the group consisting of halogen, nitro, amino, $C_{1-6}$ alkyl, $C_{3-8}$ cycloalkyl, cyano, $C_{1-6}$ alkoxy [or] *and* $C_{6-10}$ aryloxy; $R_1$ is hydrogen, $C_{1-6}$ alkyl, $C_{3-8}$ cycloalkyl or $C_{6-10}$ aryl[.]; *and X is O or S.*

AS A RESULT OF REEXAMINATION, IT HAS BEEN DETERMINED THAT:

The patentability of claims 12 and 18–19 is confirmed.

Claim 7 is cancelled.

Claims 1–5 are determined to be patentable as amended.

Claims 6, 8–11 and 13–17, dependent on an amended claim, are determined to be patentable.

New claims 20–33 are added and determined to be patentable.

1. A method of treating or ameliorating pain in a mammal, comprising administering to a mammal in need of such treatment an effective amount of a compound having the Formula II:

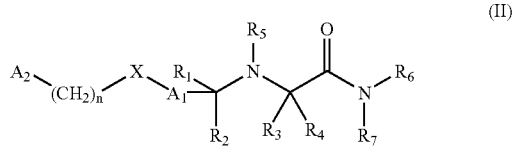

(II)

or a pharmaceutically acceptable salt or prodrug thereof, wherein:

$R_1$, $R_2$, $R_3$ and $R_4$ are independently hydrogen, alkyl, cycloalkyl, alkenyl, alkynyl, haloalkyl, aryl, aminoalkyl, hydroxyalkyl, alkoxyalkyl or carboxyalkyl;

$R_5$, $R_6$ and $R_7$ are independently hydrogen, alkyl, cycloalkyl, alkenyl, alkynyl, haloalkyl, aryl, aminoalkyl, hydroxyalkyl, alkoxyalkyl or carboxyalkyl, or $R_5$, is defined as above, and $R_6$ and $R_7$ together with the nitrogen atom to which they are attached form a heterocycle selected from the group consisting of piperidinyl, piperizinyl, pyrrolidinyl, imidazolidinyl, imidazolinyl, indolinyl, isoindolinyl, morpholinyl, pyrazolidinyl and pyrazolinyl;

$A_1$ and $A_2$ are independently aryl, saturated carbocyclic or partially unsaturated carbocyclic, any of which is optionally substituted with any one substituent from the group consisting of halo, haloalkyl, aryl, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, hydroxyalkyl, aminoalkyl, carboxyalkyl, alkoxyalkyl, nitro, amino, ureido, cyano, alkanoylamino, hydroxy, thiol, alkanoyloxy, azido, alkoxy, carboxy, aminocarbonyl, and alkylthiol, wherein optionally substituted heteroaryl is selected from the group consisting of thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbazolyl, carbazolyl, β-carbolinyl, phenanthridinyl, acrindinyl, perimidinyl, phenathrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyromidin-4-one, 1,2- benzoisoxazol-3-yl, 4-nitrobenzofurazan, benzimidazolyl, 2-oxindolyl and 2-oxobenzimidazolyl;

X is one [or] *of* O, S, $NR_8$, $CH_2$, C(O), $NR_8C(O)$, $C(O)NR_8$, SO, $SO_2$ or a covalent bond; where $R_8$ hydrogen, alkyl, cycloalkyl, alkenyl, alkynyl, haloalkyl, aryl, aminoalkyl, hydroxyalkyl, alkoxyalkyl or carboxyyalkyl; and n is 0, 1, 2 or 3.

2. The method according to claim 1, wherein $A_1$ [nd] *and* $A_2$ are both optionally substituted aryl moieties.

3. [The] *A* method [according to claim 1] *of treating or ameliorating pain in a mammal, comprising administering to a mammal in need of such treatment an effective amount of a compound having the Formula II*:

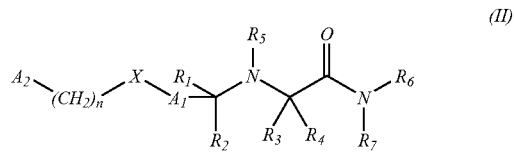

(II)

*or a pharmaceutically acceptable salt thereof, wherein*:

$A_1$ *and* $A_2$ *are phenyl moieties, wherein* $A_2$ *is optionally substituted by one or two substituents independently selected from the group consisting of hydrogen*, $C_{1-6}$ *alkyl, halogen, hydroxy,* $C_{1-4}$ *alkoxy and trifluoromethyl*;

$R_1$ *and* $R_2$ *are hydrogen*;

$R_3$ *and* $R_4$ *are methyl*;

$R_5$, $R_6$ *and* $R_7$ *are independently hydrogen,* $C_{1-6}$ *alkyl, or* $C_{3-7}$ *cycloalkyl;* [and]

X *is O, S, $CH_2$, or NH; and* n *is 0, 1, 2 or 3.*

4. [The] *A* method [according to claim 1] *of treating or ameliorating pain in a mammal, comprising administering to a mammal in need of such treatment an effective amount* of a compound, or a pharmaceutically acceptable salt thereof, wherein said compound is selected from the group consisting of:

2-(4-(2-fluorobenzyloxy)benzylamino)-2-methyl-propanamide;

2-(4-(4-fluorophenoxy)benzylamino)-2-methyl-propanamide;

2-(4-cyclohexyloxybenzylamino)-2-methyl-propanamide;

2-(4-(5,6,7,8-tetrahydro-2-naphthoxy)benzylamino)-2-methyl-propanamide;

2-(4-(2-adamantanoxy)benzylamino)-2-methyl-propanamide;

2-(4-(4-chloro-2-fluorophenoxy)benzylamino)-2-methyl-propanamide;

2-(4-(2,4-difluorophenoxy)benzylamino)-2-methyl-propanamide;

2-(4-(3,4-difluorophenoxy)benzylamino)-2-methyl-propanamide;

2-(4-(6-bromo-4-fluorophenoxy)benzylamino)-2-methyl-propanamide;

2-(4-(4-nitrophenoxy)benzylamino)-2-methyl-propanamide;

2-(4-(3,5-difluorophenoxy)benzylamino)-2-methyl-propanamide, 2-(4-(4-cholorophenoxy)benzylamino)-2-methyl-propanamide;

2-(4-(4-methylphenoxy)benzylamino)-2-methyl-propanamide;

2-(4-(2-chloro-4-fluorophenoxy)benzylamino)-2-methyl-propanamide;

2-(4-cycloheptoxybenzylamino)-2-methyl-propanamide;

2-(4-(exo-2-norbornoxy)benzylamino)-2-methyl-propanamide;

2-(3-fluoro-4-(4-fluorophenyl)benzylamino)-2-methyl-propanamide; and 2-(4-(N, N-diphenylamino)benzylamino)-2-methyl-propanamide.

5. A method for treating, preventing or ameliorating pain; providing local anesthesia; or treating arrhythmias, comprising administering to a mammal in need of such treatment an effective amount of a compound having the Formula II:

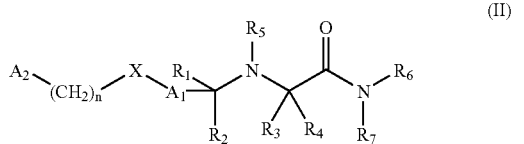

(II)

or a pharmaceutically acceptable salt or prodrug thereof, wherein:

$R_1$, $R_2$, $R_3$ and $R_4$ are independently hydrogen, alkyl, cycloakyl, alkenyl, alkynyl, haloalkyl, aryl, aminoalkyl, hydroxyalkyl, alkoxyyalkyl or carboxyyalkyl;

$R_5$, $R_6$ and $R_7$ are independently hydrogen, alkyl, cycloalkyl, alkenyl, alkenyl, alkynyl, haloalkyl, aryl, aminoalkyl, hydroxyalkyl, alkoxyalkyl or carboxyalkyl, or $R_5$, is defined as above, and $R_6$ and $R_7$ together with the nitrogen atom to which they are attached form a heterocycle selected from the group consisting of piperidinyl, piperizinyl, pyrrolidinyl, imidazolidinyl, imidazolinyl, indolinyl, isoindolinyl, pyrazolidinyl and pyrazolinyl;

$A_1$ and $A_2$ are independently aryl, saturated carbocyclic or partially unsaturated carbocyclic, any of which is optionally substituted with any one substituent from the group consisting of halo, haloalkyl, aryl, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, hydroxyalkyl, aminoalkyl, carboxyalkyl, alkoxyalkyl, nitro, amino, ureido, cyano, alkanoylamino, hydroxy, thiol, alkanoyloxy, azido, alkoxy, carboxy, aminocarbonyl, and alkythiol, wherein optionally substituted heteroaryl is selected from the group consisting the thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbazolyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, 4-nirobenzofurazan, benzimidazolyl, 2-oxindolyl and 2-oxobenzimidazolyl;

X is one [or] of O, S, $NR_8$, $CH_2$, C(O), $NR_8C(O)$, $C(O)NR_8$, SO, $SO_2$ or a covalent bond; where $R_8$ is hydrogen, alkyl, cycloalkyl, alkenyl, alkynyl, haloalkyl, aryl, aminoalkyl, hydroxyalkyl, alkoxyalkyl or carboxyalkyl; and n is 0, 1, 2 or 3;

provided that when X is O, S, $Ch_2$ or NH; $R_1$ and $R_2$ are hydrogen, $R_3$ and $R_4$ are methyl or ethyl, then at least one of $A_1$ and $A_2$ is other than unsubstituted or substituted phenyl.

20. *A method of treating or ameliorating pain in a mammal, comprising administering to a mammal in need of such treatment an effective amount of a compound having the Formula II:*

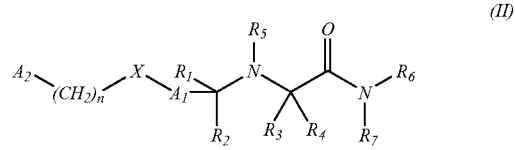

(II)

*or a pharmaceutically acceptable salt thereof, wherein:*

$A_1$ *and* $A_2$ *are both phenyl moieties, wherein* $A_1$ *and* $A_2$ *are each optionally independently substituted by one or two substituents independently selected from the group consisting of halogen, nitro, amino, $C_{1-6}$ alkyl, $C_{3-8}$ cycloalkyl, cyano, $C_{1-6}$ alkoxy and $C_{6-10}$ aryloxy;*

$R_1$ *is hydrogen, $C_{1-6}$ alkyl, $C_{3-8}$ cycloalkyl or $C_{6-10}$ aryl;*

$R_2$, $R_3$ *and* $R_4$ *are independently hydrogen, alkyl, cycloalkyl, akenyl, alkynyl, haloalkyl, aryl, aminoalkyl, hydroxyalkyl, alkoxyakyl, or carboxyalkyl;*

$R_5$, $R_6$ *and* $R_7$ *are independently hydrogen, alkyl, cycloalkyl, alkenyl, alkynyl, haloalkyl, aryl, aminoalkyl, hydroxyalkyl, alkoxyakyl, or carboxyalkyl; or $R_5$, is defined as above, and $R_6$ and $R_7$ together with the nitrogen atom to which they are attached form a* heterocycle selected from the group consisting of piperidinyl, piperizinyl, pyrrolidinyl, imidazolidinyl, imidazolinyl, indolinyl, isoindolinyl, morpholinyl, pyrazolidinyl and pyrazolinyl;

X is O or S; and n is 0, 1, 2 or 3.

21. The method according to claim 2, wherein X is O or S.

22. The method according to claim 2, wherein:

$R_1$ and $R_2$ are independently hydrogen, methyl or ethyl; and $R_3$ and $R_4$ are independently hydrogen or $C_{1-4}$ alkyl.

23. The method according to claim 2, wherein $R_5$, $R_6$, and $R_7$ are independently hydrogen or $C_{1-4}$ alkyl.

24. The method according to claim 2, wherein:

$R_1$ and $R_2$ are independently hydrogen, methyl or ethyl;

$R_3$ and $R_4$ are independently hydrogen or $C_{1-4}$ alkyl;

$R_5$, $R_6$ and $R_7$ are independently hydrogen or $C_{1-4}$ alkyl; and

X is O or S.

25. The method according to claim 20, wherein $A_1$ and $A_2$ are each phenyl optionally independently substituted by one or two substituents independently selected from the group consisting of halogen.

26. The method according to claim 20, wherein $R_1$ and $R_2$ are independently hydrogen, methyl or ethyl.

27. The method according to claim 20, wherein $R_3$ and $R_4$ are independently hydrogen or $C_{1-4}$ alkyl.

28. The method according to claim 20, wherein $R_5$, $R_6$, and $R_7$ are independently hydrogen or $C_{1-4}$ alkyl.

29. The method according to claim 20, wherein n is 0 or 1.

30. The method according to claim 20, wherein X is O.

31. The method according to claim 20, wherein:

$A_1$ and $A_2$ are each phenyl optionally independently substituted by one or two substituents independently selected from the group consisting of halogen;

$R_1$ and $R_2$ are independently hydrogen, methyl or ethyl;

$R_3$ and $R_4$ are independently hydrogen or $C_{1-4}$ alkyl;

$R_5$, $R_6$, and $R_7$ are independently hydrogen or $C_{1-4}$ alkyl;

n is 0 or 1; and

X is O.

32. The method according to claim 31, wherein $A_1$ is unsubstituted phenyl, and $A_2$ is phenyl substituted once by halogen.

33. The method according to claim 31, wherein $A_1$ is unsubstituted phenyl, and $A_2$ is phenyl substituted once by fluoro.

* * * * *